United States Patent [19]

Matsumura et al.

[11] Patent Number: 4,529,722
[45] Date of Patent: Jul. 16, 1985

[54] OXACEPHALOSPORIN DERIVATIVES

[75] Inventors: Hiromu Matsumura, Ashiya; Toshisada Yano, Kobe; Masayuki Narisada, Ibaraki, all of Japan

[73] Assignee: Shionogi & Co., Ltd., Osaka, Japan

[21] Appl. No.: 559,293

[22] Filed: Dec. 5, 1983

[30] Foreign Application Priority Data

Dec. 6, 1982 [JP] Japan ................. 57-214112

[51] Int. Cl.$^3$ .................. A61K 31/535; C07D 498/04
[52] U.S. Cl. ...................... 514/210; 544/90
[58] Field of Search .............. 544/90; 424/248.51, 424/248.52

[56] References Cited

U.S. PATENT DOCUMENTS

| | | | |
|---|---|---|---|
| 4,013,653 | 3/1977 | Wolfe | 544/90 |
| 4,232,151 | 11/1980 | Nagata et al. | 544/90 |
| 4,371,532 | 2/1983 | Narisada et al. | 424/248.51 |

FOREIGN PATENT DOCUMENTS 1455017 11/1976 United Kingdom.
1574791 9/1980 United Kingdom.

OTHER PUBLICATIONS

Cama et al., J. Am. Chem. Soc., 96:24, Nov. 27, 1974, pp. 7582–7584.
Narisada et al., J. Med. Chem., vol. 22, No. 7, Jul. 1979, pp. 757–759.
Wolfe et al., Can. J. Chem., vol. 52, (1974), pp. 3996–3999.

*Primary Examiner*—Richard L. Raymond
*Attorney, Agent, or Firm*—Wenderoth, Lind & Ponack

[57] ABSTRACT

A 7β-ureidoacetamido-7α-methoxy-3-[1-(2-hydroxyethyl)-1H-tetrazol-5-yl]thiomethyl-1-dethia-1-oxa-3-cephem-4-carboxylic acid derivative represented by the following formula:

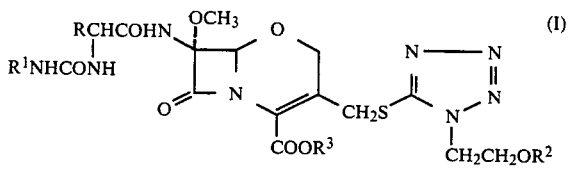

wherein R is aryl or heteroaryl; $R^1$ is hydrogen or alkyl optionally substituted by halogen or pyridinium; $R^2$ is hydrogen or a hydroxy-protecting group; and $R^3$ is hydrogen, a light metal, or a carboxy-protecting group.

9 Claims, No Drawings

OXACEPHALOSPORIN DERIVATIVES

The present invention relates to 7β-ureidoacetamido-7α-methoxy-3-[1-(2-hydroxyethyl)-1H-tetrazol-5-yl]thiomethyl-1-dethia-1-oxa-3-cephem-4-carboxylic acid derivatives represented by the formula (I) below, their therapeutical use, processes for preparing them and pharmaceutical compositions containing them:

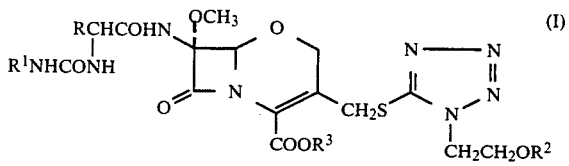

wherein R is aryl or heteroaryl; $R^1$ is hydrogen or alkyl optionally substituted by halogen or pyridinium; $R^2$ is hydrogen or a hydroxy-protecting group; and $R^3$ is hydrogen, a light metal, or a carboxy-protecting group.

In this specification, preferable ranges of the terms are as follows:

The term "aryl" refers to phenyl, hydroxyphenyl and the like, and the term "heteroaryl" refers to furyl, thienyl, 2-aminothiazolyl and the like.

The term "alkyl optionally substituted by halogen" refers to $C_1$–$C_3$ primary alkyl optionally substituted by chloro, bromo, iodo or fluoro.

The term "hydroxy-protecting group" refers to an ether residue such as methoxymethyl, tetrahydropyranyl and the like, or an acyl group such as tert.-butoxycarbonyl, carbobenzoxy, chloroacetyl, dichloroacetyl and the like.

The term "light metal" denotes a metal belonging to the second to forth period of the groups I to III in the periodic table, which provides a physiologically acceptable ion in the body fluid. Lithium, sodium, potassium, magnesium and calcium are representative of the light metal.

The term "carboxy-protecting group" refers to those commonly employed in the cephalosporin art to protect the carboxyl group at the 4-position without adversely affecting the β-lactam ring. Illustrative of these protecting groups are alkyl and aralkyl each optionally substituted by nitro, alkoxy, aryl, halogen or acyloxy. Specific examples are p-nitrobenzyl (abbrev. PNB), p-methoxybenzyl (abbrev. PMB), benzhydryl (abbrev. BH), tert.-butyl, pivaloyloxymethyl (abbrev. POM), trichloroethyl (abbrev. TCE), etc.

The compounds (I) of the present invention exhibit a strong antibiotic activity to various microorganisms and, also to those resistant to other antibiotics. It is noteworthy that they show excellent antibiotic activity to organisms resistant to other antibiotics of penicillin or cephalosporin series.

When administered to mammals, the compounds (I) show various pharmacological characteristics with respect to absorption, distribution, metabolism and excretion, without exhibiting remarkable side-effect. Especially, they maintain a high blood level for a long period of time showing high curative ability.

Thus, the compounds (I) are valuable antibiotics against various Gram positive and negative bacteria, and useful as drugs for human and veterinary uses. They can be used for treating or preventing infections caused by Gram positive bacteria (e.g. *Staphylococcus aureus, Streptococcus pyogenes, Bacillus subtilis, Bacillus cereus, Diplococcus pneumoniae, Corynebacterium diphtheriae*) and Gram negative bacteria (e.g. *Escherichia coli, Klebsiella pneumoniae, Proteus mirabilis, Proteus vulgaris, Proteus rettgeri, Proteus morganii, Enterobacter cloacae, Shigella sonnei, Salmonella paratyphi, Salmonella typhi, Serratia marsescens*), and some are active even against anaerobic bacteria (e.g. *Bacteroides fragilis, Eubacterium lentum*). The compounds can be used also as disinfectants for preventing decay of perishables, additives to feedstuffs, or preventing bacterial growth of hygenical materials.

The compounds (I) can be used in a wide variety of oral or parenteral dosage forms solely or in admixture with other coacting substances. The pharmaceutical compositions may be a mixture of 0.01 to 99% of compound (I) with a pharmaceutical carrier which can be a solid material or liquid material in which the compounds are dissolved, dispersed, or suspended. They can be in a unit dosage form. The solid compositions can take the form of tablets, powder, dry syrups, troches, granules, capsules, pills, suppositories, or like solid preparations. The liquid compositions can take the forms of injections, ointments, dispersions, inhalant, suspensions, solutions, emulsions, syrups, or elixirs. They may be flavored, colored, and tablets, granules, and capsules may be coated.

All of diluents (e.g. starch, sucrose, lactose, calcium carbonate, kaolin); bulking agents (e.g. lactose, sugar, salt, glycine, starch, calcium carbonate, calcium phosphate, kaolin, bentonite, talc, sorbitol); binders (e.g. starch, acacia, gelatin, glucose, sodium alginate, tragacanth, carboxymethylcellulose, syrup, sorbitol, polyvinylpyrrolidone); disintegrators (e.g. starch, agar, carbonates, sodium laurylsulfate); lubricant (e.g. stearic acid, talc, paraffin, boric acid, silica, sodium benzoate, polyethylene glycol, cacao oil, magnesium stearate); emulsifying agents (e.g. lecithin, sorbitan monooleate, acacia); suspending agents (e.g. sorbitol, methyl cellulose, glucose, sugar syrup, gelatin, hydroxyethylcellulose, carboxymethylcellulose, aluminum stearate gel, hydrogenated fats); solvents (e.g. water, buffer, peanut oil, sesame oil, methyl oleate); preservatives (e.g. methyl or ethyl p-hydroxybenzoate, sorbic acid); edible coloring agents, aromatic substances, solubilizing agents, buffers, stabilizing agents, analgesics, dispersing agents, wetting agents, antioxidants, and the like can be used if the agents do not exert adverse effect on the compounds, according to the methods conventional in the art.

Compounds (I) having a carboxylic acid salt group are soluble in water, and conveniently used as solution for intravenus, intramuscular, or subcutaneous injection according to a conventional method. The compounds can be dissolved in aqueous or oily solvents for injection to give a solution in an ampoule, but generally, more prolonged storage are possible by making a vial preparation containing crystals, powder, microcrystals, or lyophilizate of compound (I), and dissolving or suspending the drug before use with the said solvents for injection. The vial preparation or injection can be given to a patient at a daily dose of e.g. 0.2 to 5 g depending on the infected bacteria, condition of the patient, and interval of the administration.

Compounds (I), being a pharmaceutically acceptable ester (e.g. indanyl, acetoxymethyl, pivaloyloxymethyl, ethoxycarbonyloxyethyl, phenacyl, phthalidyl, phenyl, tolyl, xylyl, methoxyphenyl esters), can be absorbed through the digestive organ to some extent, and can be administered to human or veterinary subjects as powder, tablets, granules, capsules, dry syrup, emulsions, solution, suspension, and like oral preparations. They may be pure compounds or a composition comprising compounds (I) and said pharmaceutical carriers. The preparation can be made according to the methods conventional in the art, and can be administered to a patient as a daily dose of e.g. 1 to 2 g depending on the condition of patient and the diseases.

Further, compounds (I) can be used as suppositories, ointments for topical or ocular use, powders for topical use, and like preparations preparable according to methods well known to those skilled in the art. The preparation can contain 0.01 to 99% of the compound (I) together with a necessary amount of pharmaceutical carrier given above. A necessary amount e.g. 1 μg to 1 mg of the preparation can be applied to the affected part.

This invention also provides a method for treating or preventing human or veterinary bacterial infections by administering to the human or animal subject an effective amount of compound (I) at a daily dose of e.g. 0.2 to 5 g for injection or e.g. 1 to 2 g for oral administration, or 1 μg to 1 mg for topical application, at an interval of e.g. 3 to 12 hours.

The method is applicable for treating or preventing some diseases caused by bacteria sensitive to compounds (I) e.g. pneumonia, bronchitis, pneumonitis, empyema, nasopharyngitis, tonsillitis, rhinitis, dermatitis, pustulosis, ulceration, abses, wound and soft tissue infections, ear infections, osteomyelitis, septicemia, gastroenteritis, enteritis, urinary tract infectitons, and pyelonephritis when caused by bacteria sensitive to compound (I).

Preferably the compounds (I) are given to a patient in forms of pharmaceutical preparations e.g. powder, dry syrup, tablets, traches, granules, capsules, pills, suppositories, injections, ointments, dispersions, inhalent, suspensions, solutions, emulsions, syrups, and elixirs. They may be in a unit dosage form e.g. tablets, troches, capsules, injections, vials, granules or powder in a separate container or package.

All of the pharmaceutical preparations listed above can be prepared in a conventional manner.

It will be readily understood to those in the art that the compounds (I) can also be used as germicides or anticeptics. In addition, they are useful as a starting material for preparing some other compounds of the formula (I) and as an antibiotic agent for testing the sensitivity of microorganisms.

Preferred compounds (I) of the invention are those wherein R is phenyl, hydroxyphenyl, furyl or thienyl, $R^1$ is hydrogen, methyl, ethyl or 2-chloroethyl, $R^2$ is hydrogen, benzyloxycarbonyl, p-methylbenzyloxycarbonyl, acetyl or haloacetyl, and $R^3$ is hydrogen, sodium, potassium, diphenylmethyl, acetoxymethyl, 1-(ethoxycarbonyloxy)ethyl or pivaloyloxymethyl.

The compounds of the formula (I) can be prepared by various methods detailed below:

1. PREPARATION OF SALTS

The reaction of the compound (I) wherein $R^3$ is hydrogen with a base or a salt of a weaker carboxylic acid results in the compound (I) wherein $R^3$ is a light metal. The reaction may be carried out according to a conventional method known to the art. Preferred methods are the neutralization of the free acid (I) with a metal bicarbonate. Alternative method is the exchange reaction of the free acid (I) with a salt of a lower carboxylic acid in a polar organic solvent such as alcohol, ketone or ester, followed by the addition of a solvent to which the desired salt (I) is sparingly soluble.

The above reactions complete after one to ten minutes when carried out at a temperature below 50° C. If necessary, the reaction mixture can be kept for a longer time unless any side reaction occurs.

2. ELIMINATION OF CARBOXY-PROTECTING GROUP

The compounds of the formula (I) wherein $R^3$ is a carboxy-protecting group can be converted to the compounds (I) wherein $R^3$ is hydrogen according to any of the conventional deprotecting reactions described below.

In the following description, the carboxy-protecting group will be sometimes represented by the name corresponding to the group formed by the reaction between the carboxylic acid and the compound employed for protecting the carboxylic acid, only for the purpose of avoiding the complexity of description. Thus, the protecting group "$R^3$" contained in the moiety of the formula:

$$-COOR^3$$

will be referred to as "ester" for convenience.

(a) The compounds (I) having highly reactive protecting groups can be deprotected by contact with an acid, a base, a buffer or an ion exchange resin in an aqueous solution. Less reactive protecting group such as trichloroethyl or p-nitrobenzyl can be eliminated by treating it with a combination of a metal and a acid or with dithionate, or by a catalytic reduction.

(b) Aralkyl esters can be eliminated by a hydrogenation using, e.g., platinum, palladium or nickel as a catalyst.

(c) Aralkyl esters and cyclopropylmethyl esters can be eliminated through solvolysis using a mineral acid, a Lewis acid such as aluminum chloride, tin chloride and titanium tetrachloride, a sulfonic acid such as methanesulfonic acid and trifluoromethanesulfonic acid, or a strong carboxylic acid such as trifluoroacetic acid, and if necessary, in the presence of a cation scavenger.

(d) The other conventional processes known for deprotecting carboxy-protecting groups can be employed in the present invention.

3. INTRODUCTION OF A TETRAZOLYLTHIO GROUP

The compounds (I) of the invention can be obtained by the reaction between the compound represented by the formula (II) below and the substituted tetrazole-5-thiol of the formula (III) or its reactive derivative;

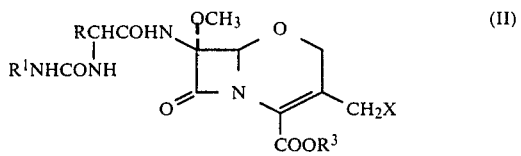

$$\underset{\underset{CH_2CH_2OR^2}{|}}{\overset{N\overline{\phantom{xx}}N}{HS}\diagdown\overset{\parallel}{\underset{N}{C}}\diagup\overset{N}{\underset{N}{\diagdown}}}\quad (III)$$

wherein R, $R^1$, $R^2$ and $R^3$ are as defined above and X is a leaving group. Preferred leaving groups are halogen and acyloxy having a high activity such as sulfonyloxy. The preferred reactive derivatives of the tetrazole-5-thiol are an alkali metal salt and an ammonium salt of the thiol (III).

4. AMIDATION

The compounds of the formula (I) can be prepared by reacting the amine compound of the formula (IV):

(IV)

wherein $R^2$ and $R^3$ are as defined above, or a reactive derivative thereof with a substituted acetic acid of the formula (V):

$$\underset{NHCONHR^1}{\overset{RCHCOOH}{|}}\quad (V)$$

wherein R and $R^1$ are as defined above, or a reactive derivative thereof.

The reaction between the compound (IV) and the compound (V) is conducted in different manners as explained below depending on the nature of the reactants.

(a) FREE ACIDS

The amine (IV) or its derivative is reacted with the properly substituted acetic acid (V) or its derivative in the presence of a condensing agent, such as carbodiimides, carbonyldiimidazole, isoxazolium salts, acylamino compounds, phosphorus halogenides, cyanuric halogenides, enzymes for amidation, etc., to give the compound (I) of the invention.

(b) ACID ANHYDRIDE DERIVATIVES

The acid anhydride derivative of the compound (V) can be reacted with the amine (IV) in the presence of an acid scavenger such as an organic or inorganic base, oxirane, an amide, an adsorbent, or the like, to give the compound (I). The acid anhydrides employed in the reaction include symmetric anhydrides of the acids (V), mixed anhydrides of the acid (V) with either a mineral acid or an organic acid such as other carboxylic acid or sulfonic acid, intramolecular anhydrides such as ketenes, etc.

(c) ACID HALIDE DERIVATIVES

The acid halide derivative of the compound (V) can be reacted with the amine (IV) or its reactive derivative in the presence of an acid scavenger selected from those mentioned in the above item (b) to give the compound (I). An aqueous solvent can be employed in this reaction.

(d) ACTIVATED ESTER AND AMIDE DERIVATIVES

The activated ester or amide derivative of the compound (V) is reacted with the amine (IV) in an organic solvent, preferably in an aprotic organic solvent, to obtain the compound (I).

Examples of the activated esters and amides employed in this reaction are enol esters, aryl esters, esters formed with a hydroxy heterocycle containing nitrogen atom(s) in the ring, esters formed with an N-hydroxy compound, thiol esters, amides formed with a heterocycle such as imidazole, amides formed with 2-alkoxy-1,2-dihydroquinoline, diacylanilides, formimino compounds, etc.

Other conventional amidation reactions known per se can be employed for the preparation of the compounds (I).

In the above reactions stated in 4-(a) to (d), typical reactive derivatives of the amine (II) are those wherein the amino group at the 7-position has been activated by a silyl radical such as trialkylsilyl or alkoxydialkylsilyl, a metal oxycarbonyl radical, an alkoxyphosphinyl radical, an enamine radical, etc. In addition, the reactive derivatives include the amines (II) wherein the amino group has been substituted by 1-haloalkylidene, 1-alkoxyalkylidene, 1-haloaralkylidene, 1-alkoxyaralkylidene, 1-acyloxyaralkylidene, alkylidene or substituted alkenyl radical.

5. UREIDE FORMATION

The compounds (I) of the invention can also be obtained by treating the compound of the formula (VI) with a carbamoyl halide of the formula (VII-a) or an isocyanate of the formula (VII-b):

(VI)

$R^1NHCOHal$ (VII-a)  $R^1NCO$ (VII-b)

wherein R, $R^1$, $R^2$ and $R^3$ are as defined above and Hal is halogen.

6. MODIFICATION OF SUBSTITUENT ON TETRAZOLE RING

The compounds (I) of the invention wherein $R^2$ is an ether residue can be converted to the compound (I) wherein $R^2$ is hydrogen by treating with an acid. Likewise, the compound (I) wherein $R^2$ is an ester residue can be converted to the carboxylic acid (I) by treating with a base.

7. PROTECTION OF CARBOXYLIC ACID AND OTHER REACTIVE FUNCTIONAL GROUPS

In carrying out the foregoing various reactions or in converting the compound (I) to the other compound (I), it may be sometimes necessary to protect reactive functional groups other than the reacting group involving in the intended reaction.

For this purpose, a variety of conventional techniques for the protection are all applicable to the processes of the invention. Such techniques are, for example, disclosed in the literatures, such as J. F. W. McOmie Ed., "Protective Groups in Organic Chemistry", pp183, PLEUM Press, N.Y., 1973; S. Patai, Ed., "The Chemistry of Functional Groups", pp505, Interscience Publ., John Wiley & Sons Ltd. London, 1969; and Flynn Ed., "Cephalosporins and Penicillins", Academic Press, N.Y. 1972. Typical examples of the protection of reactive functional groups are acylation and etherification for a hydroxyl group, acylation, enamination and silylation for an amino group, and esterification, amidation and acid anhydridation for a carboxylic acid.

It should be noted that the term "protection of carboxylic acid" herein used also refers to the esterification of the carboxylic acid at 4-position for the purpose of obtaining a pharmacologically active ester. The esterification of the compound (I) having a free carboxylic acid can be conducted by neutralizing the acid with a base to form a carboxylate, and treating the latter with an acid halide having a proper ester residue.

8. REACTION CONDITIONS

Most of the reactions listed in the above items 1. to 7. are usually carried out at a temperature between −30° and 100° C., particularly, between −20° and 50° C., for 10 minutes to 10 hours in a proper solvent, and if necessary, under anhydrous conditions.

Examples of the solvent employable in the processes of this invention are the following: hydrocarbons (e.g. pentane, hexane, octane, benzene, toluene, xylene), halogenated hydrocarbons (e.g. dichloromethane, chloroform, carbon tetrachloride, dichloroethane, trichloroethane, chlorobenzene), ethers (e.g. diethylether, methyl isobutyl ether, dioxane, tetrahydrofuran), ketones (e.g. acetone, methyl ethyl ketone, cyclohexanone), esters (e.g. ethyl acetate, isobutyl acetate, methyl benzoate), nitro hydrocarbons (e.g. nitromethane, nitrobenzene), nitriles (e.g. acetonitrile, benzonitrile), amides (e.g. formamide, acetamide, dimethylformamide, dimethylacetamide, hexamethylphosphorotriamide), sulfoxides (e.g. dimethyl sulfoxide), carboxylic acids (e.g. formic acid, acetic acid, propionic acid), organic bases (e.g. diethylamine, triethylamine, pyridine, picoline, collidine, quinoline), alcohols (e.g. methanol, ethanol, propanol, hexanol, octanol, benzyl alcohol), water, other industrially available solvents and a mixture thereof.

An ultimate product (I) of the invention can be isolated from the reaction mixture by any of, or a combination of, the conventional methods such as absorption, elution, distillation, precipitation, concentration, chromatography and the like, after the removal of impurities such as starting materials, by-products and solvents by conventional techniques such as extraction, evaporation, washing, filtration, drying, etc.

Specific preferred examples of the compounds (I) of the invention are:

diphenylmethyl 7β-[2-ureido-2-(2-thienyl)acetamido]-7α-methoxy-3-[1-(2-benzyloxycarbonyloxyethyl)-5-1H-tetrazolyl]thiomethyl-1-dethia-1-oxa-3-cephem-4-carboxylate, 7β-[2-ureido-2-(2-thienyl)acetamido]-7α-methoxy-3-[1-(2-hydroxyethyl)-5-1H-tetrazolyl]thiomethyl-1-dethia-1-oxa-3-cephem-4-carboxylic acid, diphenylmethyl 7β-[2-(3-methylureido)-2-(2-carbobenzoxyaminothiazol-4-yl)acetamido]-7α-methoxy-3-[1-(2-p-methylbenzyloxycarbonyloxyethyl)-5-1H-tetrazolyl]thiomethyl-1-dethia-1-oxa-3-cephem-4-carboxylate, 7β-[2-(3-methylureido)-2-(2-aminothiazol-4-yl)acetamido]-7α-methoxy-3-[1-(2-hydroxyethyl)-5-1H-tetrazolyl]thiomethyl-1-dethia-1-oxa-3-cephem-4-carboxylic acid, diphenylmethyl 7β-[2-(3-methylureido)-2-(2-thienyl)acetamido]-7α-methoxy-3-[1-(2-p-methylbenzyloxycarbonyloxyethyl)-5-1H-tetrazolyl]thiomethyl-1-dethia-1-oxa-3-cephem-4-carboxylate, 7β-[2-(3-methylureido)-2-(2-thienyl)acetamido]-7α-methoxy-3-[1-(2-hydroxyethyl)-5-1H-tetrazolyl]thiomethyl-1-dethia-1-oxa-3-cephem-4-carboxylic acid, diphenylmethyl 7β-[2-ureido-2-(2-thienyl)acetamido]-7α-methoxy-3-[1-(2-hydroxyethyl)-5-1H-tetrazolyl[-thiomethyl-1-dethia-1-oxa-3-cephem-4-carboxylate, pivaloyloxymethyl 7β-[2-ureido-2-(2-thienyl)acetamido]-7α-methoxy-3-[1-(2-hydroxyethyl)-5-1H-tetrazolyl]thiomethyl-1-dethia-1-oxa-3-cephem-4-carboxylate, sodium 7β-(2-ureido-2-phenylacetamido)-7α-methoxy-3-[1-(2-hydroxyethyl)-5-1H-tetrazolyl]thiomethyl-1-dethia-1-oxa-3-cephem-4-carboxylate, sodium 7β-[2-ureido-2-(p-hydroxyphenyl)acetamido]-7α-methoxy-3-[1-(2-hydroxyethyl)-5-1H-tetrazolyl]thiomethyl-1-dethia-1-oxa-3-cephem-4-carboxylate, sodium 7β-[2-ureido-2-(2-furyl)acetamido]-7α-methoxy-3-[1-(2-hydroxyethyl)-5-1H-tetrazolyl]thiomethyl-1-dethia-1-oxa-3-cephem-4-carboxylate, sodium 7β-[2-ureido-2-(2-thienyl)acetamido]-7α-methoxy-3-[1-(2-hydroxyethyl)-5-1H-tetrazolyl]thiomethyl-1-dethia-1-oxa-3-cephem-4-carboxylate, p-methoxybenzyl 7β-[2-ureido-2-(2-thienyl)acetamido]-7α-methoxy-3-[1-(2-hydroxyethyl)-5-1H-tetrazolyl]thiomethyl-1-dethia-1-oxa-3-cephem-4-carboxylate, diphenylmethyl 7β-(2-ureido-2-phenylacetamido)-7α-methoxy-3-[1-(2-benzyloxycarbonyloxyethyl)-5-1H-tetrazolyl]thiomethyl-1-dethia-1-oxa-3-cephem-4-carboxylate, 7β-(2-ureido-2-phenylacetamido)-7α-methoxy-3-[1-(2-hydroxyethyl)-5-1H-tetrazolyl]thiomethyl-1-dethia-1-oxa-3-cephem-4-carboxylic acid, diphenylmethyl 7β-[2-ureido-2-(p-hydroxyphenyl)acetamido]-7α-methoxy-3-[1-(2-benzyloxycarbonyloxyethyl)-5-1H-tetrazolyl]thiomethyl-1-dethia-1-oxa-3-cephem-4-carboxylate, and sodium 7β-[2-ureido-2-(p-hydroxyphenyl)acetamido]-7α-methoxy-3-[1-(2-hydroxyethyl)-5-1H-tetrazolyl]thiomethyl-1-dethia-1-oxa-3-cephem-4-carboxylate.

Practical and presently preferred embodiments of the invention are illustratively shown in the following Examples wherein Infra Red (IR) and Nuclea Magnetic Resonance (NMR) data are reported by $\nu(cm^{-1})$ and $\delta(ppm)$ values (coupling constant J in Hz) respectively and following abbreviations are employed: Me(=methyl), Bu(=butyl), Ph(=phenyl), THF(=tetrahydrofuran), DMF(=dimethylformamide), BH(=benzhydryl), PMB(=p-methoxybenzyl), POM(=pivaloyloxymethyl), mM(=millimole).

EXAMPLE 1

Diphenylmethyl 7β-[D-2-ureido-2-(2-thienyl)acetamido]-7α-methoxy-3-[1-(2-benzyloxycarbonyloxyethyl)-5-1H-tetrazolyl]thiomethyl-1-dethia-1-oxa-3-cephem-4-carboxylate (Compound No. 3).

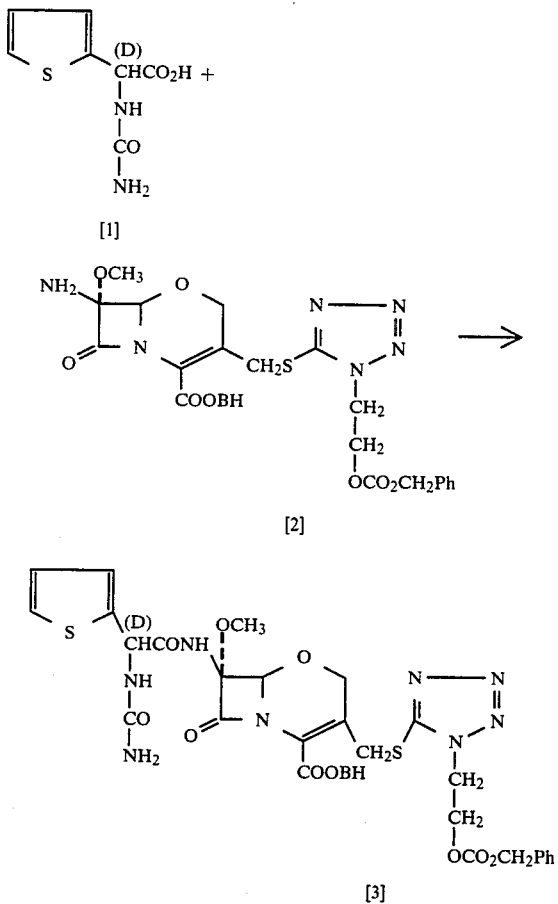

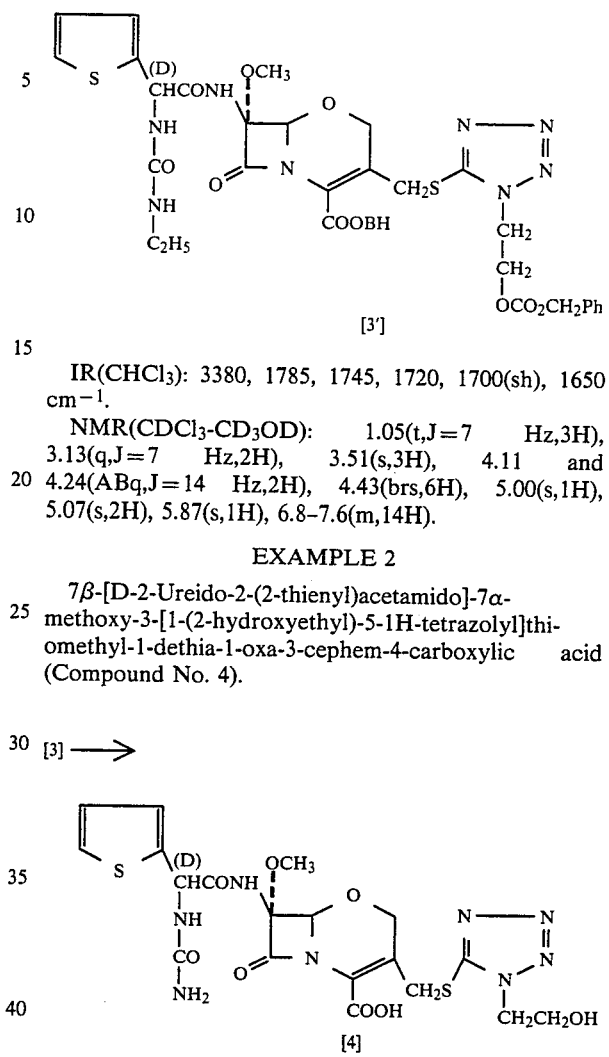

The carboxylic acid of the formula [1] (710 mg, 3.55 mM) is suspended in acetonitrile (10 ml). Thionyl chloride (630 mg, 5.30 mM) is then added to the stirred suspension while ice-cooling, and stirring is continued for one hour and 40 minutes. After removing the solvent under reduced pressure, the residue is dissolved in DMF (2 ml) and cooled to −45° C. To the cooled mixture is added a solution of the amine of the formula [2] (1.59 g, 2.36 mM) and propylene oxide (16 ml) dissolved in DMF (17 ml) and the mixture is stirred for 40 minutes at −45° C. and then for one hour while ice-cooling. The reaction mixture is poured into ethyl acetate, and the mixture is washed successively with dil. HCl solution, dil. aqueous $NaHCO_3$ solution, water and saturated saline and dried over anhydrous magnesium sulfate. After evaporation of the solvent from the mixture, the residue is purified by chlomatography over silica gel (100 g, water content: 10%). Fractions eluted with both a mixture of benzene and ethyl acetate (1:1) and ethyl acetate are combined, and the solvent is evaporated in vacuo to give the desired compound [3] as a powder. Yield: 1.71 g (84.7%).

Rf: 0.20 (ethyl acetate).

IR($CHCl_3$): 3460, 3360, 1780, 1745, 1720 $cm^{-1}$.

NMR($CDCl_3$): 3.47(s,3H), 4.7–3.8(m,8H), 4.95(s,1H), 5.08(s,2H), 5.8(brs,1H), 6.85(s), 7.8–6.5(m,23H).

In the same manner as stated above, diphenylmethyl 7β-[D-2-ethylureido-2-(2-thienyl)-acetamido]-7α-methoxy-3-[1-(2-benzyloxycarbonyloxyethyl)-5-1H-tetrazolyl]thiomethyl-1-dethia-1-oxa-3-cephem-4-carboxylate of the formula [3'] is obtained.

IR($CHCl_3$): 3380, 1785, 1745, 1720, 1700(sh), 1650 $cm^{-1}$.

NMR($CDCl_3$-$CD_3OD$): 1.05(t,J=7 Hz,3H), 3.13(q,J=7 Hz,2H), 3.51(s,3H), 4.11 and 4.24(ABq,J=14 Hz,2H), 4.43(brs,6H), 5.00(s,1H), 5.07(s,2H), 5.87(s,1H), 6.8–7.6(m,14H).

EXAMPLE 2

7β-[D-2-Ureido-2-(2-thienyl)acetamido]-7α-methoxy-3-[1-(2-hydroxyethyl)-5-1H-tetrazolyl]thiomethyl-1-dethia-1-oxa-3-cephem-4-carboxylic acid (Compound No. 4).

The diphenylmethyl ester [3] obtained in Example 1 (950 mg, 1.11 mM) is dissolved in methylene chloride (10 ml). To the solution is added while ice-cooling anhydrous aluminum chloride (1.06 g, 7.95 mM) dissolved in anisole (6 ml) and nitromethane (9 ml), and the mixture is stirred for 2 hours. The reaction mixture is poured into a mixture of sodium bicarbonate, ice water and ether, and the resulting precipitate is filtered off. The aqueous layer separated from the filtrate is acidified with hydrochloric acid, and the desired carboxylic acid [4] precipitates as crystals. Yield: 488 mg (79.3%). m.p.: 157°–158° C. (with decomposition).

Rf: 0.46 ($CHCl_3$/MeOH=1/1).

IR(nujol): 3450, 3300, 1775, 1720(sh), 1690, 1650 $cm^{-1}$.

NMR($CDCl_3$/d4-MeOH=1/1): 3.51(s,3H), 3.9–4.75(m,8H), 5.05(s,1H), 5.73(s,1H), 6.8–7.3(m,3H).

$[\alpha]_D^{24}$: −96.7°±1.3(c=1.018, MeOH).

Elementary Analysis ($C_{19}H_{21}O_8N_8S_2 \cdot 1.5H_2O$)

| | C | H | N | S |
|---|---|---|---|---|
| Calculated (%): | 39.31 | 4.17 | 19.30 | 11.04 |
| Found (%): | 39.52 | 4.20 | 19.46 | 11.34 |

EXAMPLE 3

Diphenylmethyl 7β-[DL-2-(3-methylureido)-2-(2-carbobenzoxyaminothiazol-4-yl)acetamido]-7α-methoxy-3-[1-(2-p-methylbenzyloxycarbonyloxyethyl)-5-1H-tetrazolyl]thiomethyl-1-dethia-1-oxa-3-cephem-4-carboxylate (Compound No. 8).

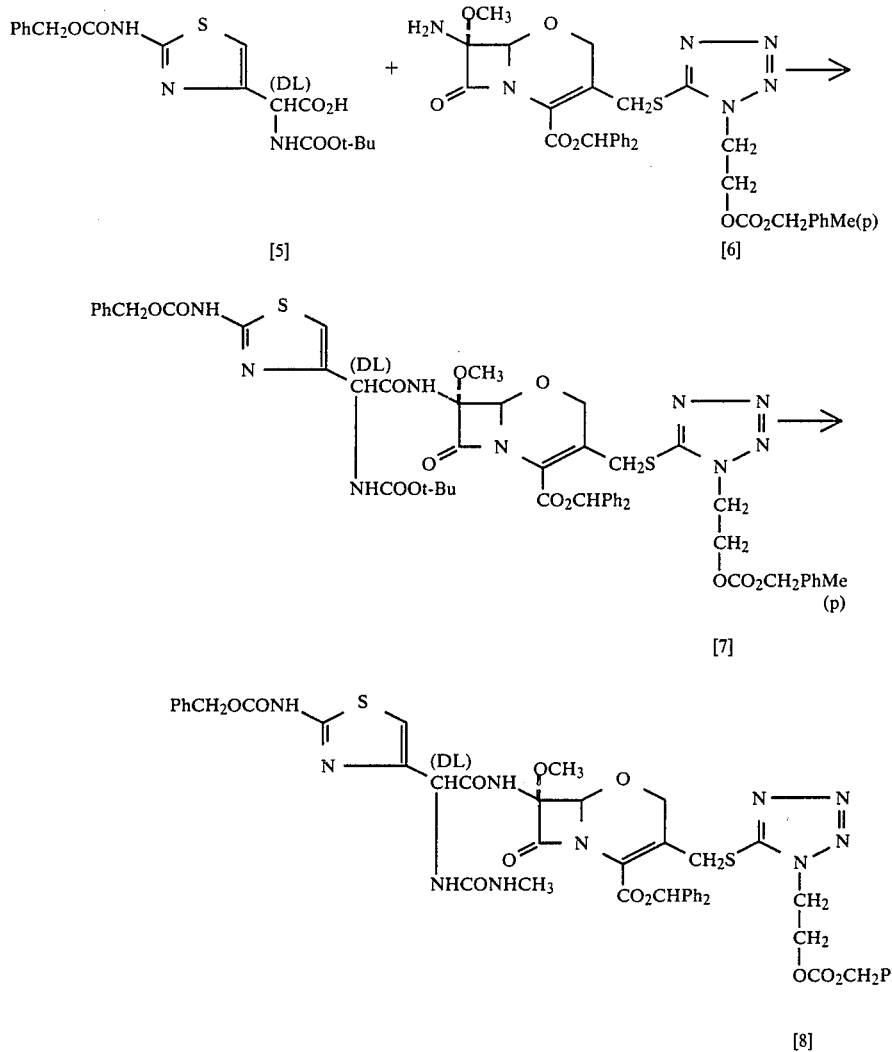

The carboxylic acid of the formula [5] (3.8 g, 10.1 mM) and the amine of the formula [6] (6.5 g, 9.46 mM) are suspended in dichloromethane (75 ml). To the mixture are added while ice-cooling pyridine (22 ml) and phosphorus oxychloride (1.32 g, 9.77 mM). After stirring for 1.5 hours, the reaction mixture is poured into ethyl acetate. The mixture is washed successively with dil.HCl, dil. NaHCO$_3$ solution, water and saturated saline and dried over anhydrous magnesium sulfate. The solvent is evaporated off, and the residue is purified by chromatography over silica gel (100 g, water content: 10%). From the fraction eluted with a mixture of benzene and ethyl acetate (3:1-1:1) the amide compound [7] is obtained. Yield: 8.25 g (86.2%).

Rf: 0.49 (benzene/ethyl acetate=1/1).

IR(CHCl$_3$): 3400, 3180, 1785, 1740(sh), 1715 cm$^{-1}$.

NMR(CDCl$_3$): 1.39(s,9H), 2.27(s,3H), 3.39(s,3H), 4.0–4.5(m,8H), 4,90(s,1H), 5.03(s,2H), 5.22(brs,2H), 5.65(brs,1H), 6.75–7.85(m,23H).

The amide compound [7] obtained above (2.5 g, 2.39 mM) is dissolved in anisole (1 ml) and trifluoroacetic acid (15 ml), and the mixture is stirred for 50 minutes. After the solvent is evaporated off under reduced pressure, the residue is triturated with ether and filtered. The crude amine trifluoroacetate thus obtained is suspended in acetonitrile (15 ml). Methyl isocyanate (2.2 ml, 37.3 mM) and triethylamine (1.5 ml) are added to the suspension while ice-cooling, and the mixture is stirred for 3 hours at room temperature. After evaporation of the solvent, the residue is dissolved in ethyl acetate, and the resulting solution is extracted with aqueous NaHCO$_3$ solution. The extract was acidified with HCl and extracted with ethyl acetate. The ethyl acetate extract is washed successively with water and saturated saline and dried over anhydrous magnesium sulfate. After removing the solvent, the powdery residue is dissolved in THF (7 ml) and dichloromethane (7 ml) and then esterified by addition of diphenyl diazomethane (Ph$_2$CN$_2$). The reaction mixture is poured into ethyl acetate, and the mixture is washed successively with dil.HCl, dil.NaHCO$_3$ solution, water and saturated saline, and dried. After evaporation of the solvent, the residue is purified by chromatography over silica gel (100 g, water content: 10%). The desired carboxylic acid of the formula [8] is obtained from the fractions eluted with a mixture of benzene and ethyl acetate (1:1) and ethyl acetate. Yield: 240 mg (10%, on the basis of the compound [6]).

Rf: 0.26 (ethyl acetate).

IR(CHCl$_3$): 3380, 1785, 1720, 1700(sh), 1670, 1650 cm$^{-1}$.

NMR(CDCl$_3$): 2.30(s,3H), 2.60(brs,3H), 3.33(split s,3H), 4.40(brs,8H), 4.90(s,1H), 5.07(s,2H), 5.20(s,2H), 6.83(s,2H), 7.1–7.4(m).

EXAMPLE 4

7β-[DL-2-(3-Methylureido)-2-(2-aminothiazol-4-yl)acetamido]-7α-methoxy-3-[1-(2-hydroxyethyl)-5-1H-tetrazolyl]thiomethyl-1-dethia-1-oxa-3-cephem-4-carboxylic acid (Compound No. 9).

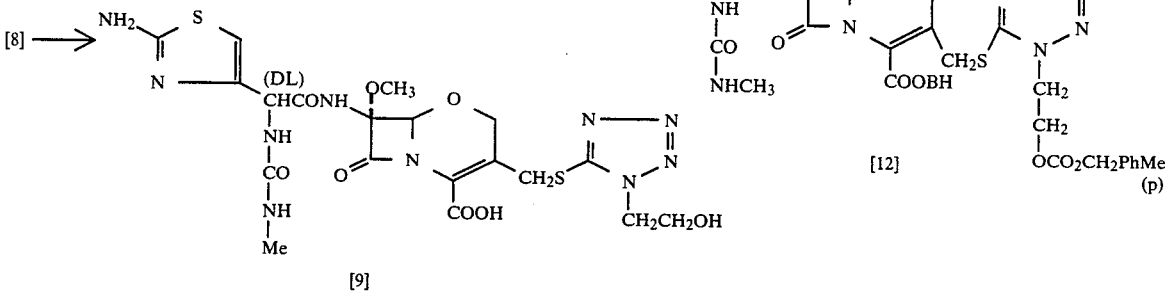

The diphenylmethyl ester [8] obtained in Example 3 (240 mg, 0.23 mM) is dissolved in dichloromethane (2 ml), and the solution is added while ice-cooling to a homogeneous solution of anhydrous aluminum chloride (500 mg, 3.75 mM) dissolved in anisole (2 ml) and nitromethane (2 ml). The mixture is stirred for 2 hours and 20 minutes and subsequently poured into a mixture of aqueous NaHCO$_3$ solution and ethyl ether while ice-cooling. Resulting precipitates are filtered off, and the aqueous phase is separated from the filtrate, acidified with hydrochloric acid, and purified by HP-20 (20 ml). Fractions eluted with a mixture of methanol and water (1:3) are combined and lyophilized to give the desired carboxylic acid [9]. Yield: 120 mg (88.9%).

Rf: 0.3 (ethyl acetate/acetic acid/water=5/1/1).

IR(KBR): 3360, 1775, 1720(sh), 1700 cm$^{-1}$.

NMR(CDCl$_3$/d4-MeOH=1/1): 2.83, 2.90(sx2,3H), 3,49, 3.45(sx,2,3H), 4.0–4.5(m), 5.00(s,1H), 5.39, 5.42(sx2,1H), 6.51, 6.54(sx2,1H).

EXAMPLE 5

Diphenylmethyl 7β-[D-2-(3-methylureido)-2-(2-thienyl)acetamido]-7α-methoxy-3-[1-(2-p-methylbenzyloxycarbonyloxyethyl)-5-1H-tetrazolyl]thiomethyl-1-dethia-1-oxa-3-cephem-4-carboxylate (Compound No. 12).

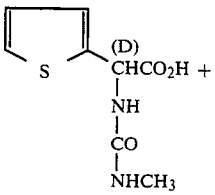

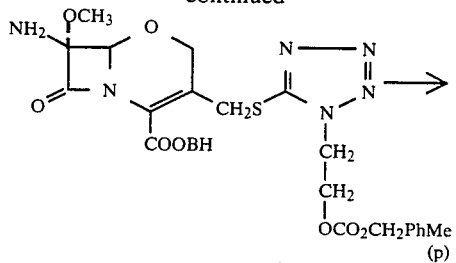

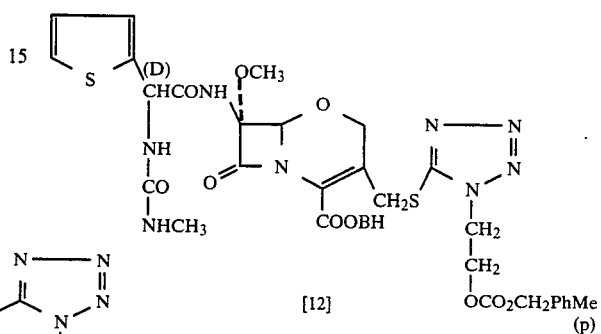

The carboxylic acid of the formula [10] (1 g, 4.67 mM) is suspended in acetonitrile (10 ml). To this stirred suspension is added thionyl chloride (1 g, 8.40 mM) while ice-cooling. Stirring is continued for one hour followed by evaporation of the solvent under reduced pressure. The residue is dissolved in DMF (5 ml) and cooled by dry ice-acetone. A solution of the amine represented by the formula [11] (2.1 g, 3.11 mM) and propylene oxide (10 ml) dissolved in DMF (10 ml) is dropwise added thereto, and the mixture is stirred for 10 minutes and allowed to stand overnight while ice-cooling. The reaction mixture is poured into ethyl acetate and washed successively with dil.HCl, dil.NaHCO$_3$ solution, water and saturated saline. After being dried over anhydrous magnesium sulfate, the mixture is evaporated to remove the solvent. The residue is purified by chromatography over silica gel (water content: 10%). From the fractions eluted with a mixture of benzene and ethyl acetate (1:1) and ethyl acetate the desired amide [12] is obtained as a powder. Yield: 1.77 g (65.5%).

Rf: 0.10 (ethyl acetate).

IR(CHCl$_3$): 3380, 1780, 1720, 1710, 1660 cm$^{-1}$.

NMR(CDCl$_3$): 2.30(s,3H), 2.60(brs,3H), 3.33 and 3.41(sx2,3H), 3.95–4.60(m,8H), 4.92 and 4.96(sx2,1H), 5.02(s,2H), 6.23(brd,J=9 Hz,1H), 6.7–7.60(m,18H).

EXAMPLE 6

7β-[D-2-(3-Methylureido)-2-(2-thienyl)acetamido]-7α-methoxy-3-[1-(2-hydroxyethyl)-5-1H-tetrazolyl]thiomethyl-1-dethia-1-oxa-3-cephem-4-carboxylic acid (Compound No. 13).

[12] ⟶

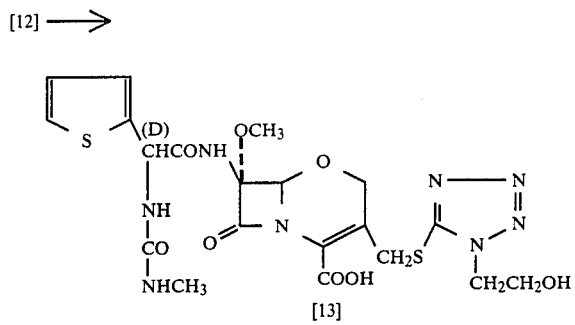

A mixture of the diphenylmethyl ester [12] (1.7 g) obtained in Example 5, anisole (0.5 ml) and trifluoroacetic acid (16 ml) is stirred for 2 hours while ice-cooling. Excessive reagents left in the reaction is removed under reduced pressure. To the residue, ethyl ether and dichloromethane are added and the mixture is agitated. The desired carboxylic acid [13] precipitates as a powder. Yield: 1.0 g (100%).

Rf: 0.27 (ethyl acetate/acetic acid/water=5/1/1).
IR(nujol): 3420, 1775, 1690, 1660(sh), 1635 cm$^{-1}$.
NMR(CDCl$_3$/CD$_3$OD=3/1): 2.70(s,3H), 3.43 and 3.49(sx2,3H), 3.80–4.85(m,8H), 5.02(s,1H), 5.76(s,1H), 6.82–7.30(m,3H).

EXAMPLE 7

Sodium 7β-[D-2-(3-methylureido)-2-(2-thienyl)acetamido]-7α-methoxy-3-[1-(2-hydroxyethyl)-5-1H-tetrazolyl]thiomethyl-1-dethia-1-oxa-3-cephem-4-carboxylate (Compound No. 14).

[13] ⟶

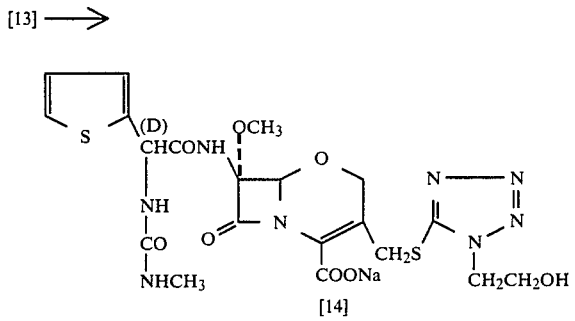

The carboxylic acid [13] (650 mg) obtained in Example 6 is dissolved in a sodium bicarbonate solution (NaHCO$_3$ 8.86 g/l H$_2$O) (10 ml). The solution is bubbled with nitrogen gas, frozen at −78° C. and lyophilized under reduced pressure to give the desired sodium salt [14] in the powdered form. Yield: 665 mg.

IR(KBr): 3440, 3350, 1765, 1660, 1605 cm$^{-1}$.
UV($\lambda_{max}^{H2O}$): 233(ε: 17130), 269(ε: 11620)nm.
NMR(D$_2$O): 3.52(s,3H), 3.9–4.6(m,8H), 5.13(s,1H), 5.67(s,1H), 6.9–7.5(m,3H).
[α]$_D^{24.5}$: −62.5°±1.0(c=1, H$_2$O).
Elementary Analysis(C$_{19}$H$_{21}$O$_8$N$_8$S$_2$Na.2H$_2$O)

|  | C | H | N | S | H$_2$O |
|---|---|---|---|---|---|
| Calculated (%): | 37.25 | 4.11 | 18.29 | 10.47 | 5.88 |
| Found (%): | 36.98 | 4.24 | 18.13 | 10.30 | 6.55 |

Minimum inhibitory concentration values of the salt [14] on *Escherichia coli* 377 strain and *E. coli* 73 strain are each 0.78γ/ml (Counting of microorganisms: 10$^8$) when measured according to the standard procedure of Nippon Kagaku Ryoho Gakkai (Japan Society of Chemotherapy).

The sodium salt [14] (665 mg) is dissolved in distilled water (4 ml) undr sterile conditions. The solution can be given to patients twice a day (daily dose is about 1 g in terms of the salt [14]) for the purpose of treating infections caused by *Staphylococcus aureus*.

Other sodium salts of the invention can be employed in the same manner as described above.

EXAMPLE 8

Diphenylmethyl 7β-[D-2-ureido-2-(2-thienyl)acetamido]-7α-methoxy-3-[1-(2-hydroxyethyl)-5-1H-tetrazolyl[thiomethyl-1-dethia-1-oxa-3-cephem-4-carboxylate (Compound No. 17)

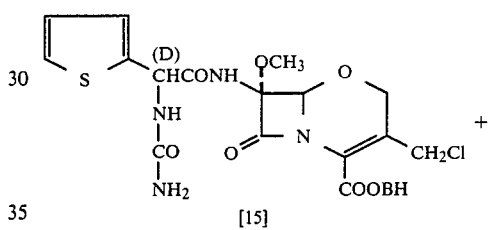

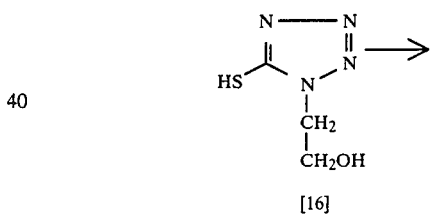

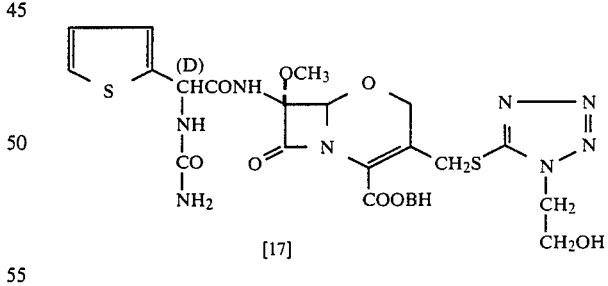

To the compound of the formula [16] (292 mg, 2 mM) dissolved in methanol (2 ml) is added sodium methylate in methanol (5.20M/l) (0.35 ml, 1.82 mM), and the mixture is stirred for five minutes while ice-cooling. The solvent is evaporated off from the mixture, and the residue containing the sodium salt of the compound [16] is dissolved in DMF (6 ml). To the DMF solution, the compound of the formula [15] (917 mg, 1.5 mM) is added at −30° C. The mixture is stirred for 20 minutes while ice-cooling. The reaction mixture is poured into ethyl acetate and successively washed with aqueous NaHCO$_3$ solution, water and saturated saline, and dried. The solvent is evaporated off and the residue is washed with ethyl ether to obtain the desired compound [17] as a powder. Yield: 984 mg (91%).

IR(nujol): 3350, 1780, 1720, 1650 cm$^{-1}$.

NMR(d6-acetone/d4-MeOH): 3.57(s,3H), 3.92(t,J=7 Hz, 2H), 4.27(brs,4H), 4.57(brs,2H), 5.07(s,1H), 5.90(s,1H), 6.92(s,1H), 7.1–7.8(m,13H).

EXAMPLE 9

Other compounds (I) prepared by the methods described in Examples 1 to 8 are listed in Table I below.

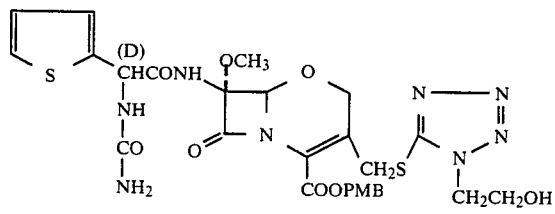

[24]

TABLE I

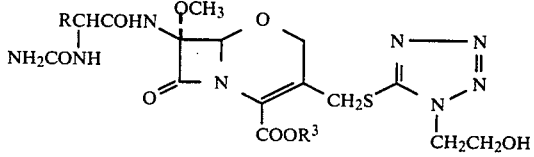

| No. | R | R$^3$ | IR | NMR |
|---|---|---|---|---|
| [18] | (2-thienyl) | POM | KBr: 3460, 3380, 1783, 1750, 1690, 1655 cm$^{-1}$. | d6-acetone: 1.20(s,9H), 3,44(s,3H), 4.00(t, J=6Hz,2H), 4.25(brs,2H), 4.38(t,J=6Hz,2H), 4.57(s,2H), 5.10(s,1H), 5.70(brs,2H), 5.89, 6.03(ABq,J=7Hz,2H), 6.79(d,J=9Hz), 6.8–7.4(m, 4H), 9.50(s,1H). |
| [19] | (phenyl) | Na | KBr: 3440, 3360, 1765, 1655, 1600 cm$^{-1}$. [α]$_D^{25}$=72.6 ± 1.1°(c= 1.013, CH$_3$OH). | D$_2$O,DSS: 3.50(s,3H), 3.8–4.6(m,2H × 4), 5.08(s, 1H), 5.37(s,1H), 7.43(brs,5H). |
| [20] | (4-hydroxyphenyl) | Na | KBr: 3440, 3360, 1765, 1655, 1605 cm$^{-1}$. | D$_2$O: 3.52(s,3H), 3.8–4.6(m,8H), 5.10(s,1H), 5.30(s,1H), 6.90(d,J=9Hz,2H), 7.33(d,J=9Hz, 2H). |
| [21] | (2-furyl) | Na | KBr: 3350, 1765, 1660, 1605 cm$^{-1}$. | D$_2$O,DSS: 3.43(s,3H), 3.9–4.6(m,2H × 4), 5.10(s, 1H), 5.67(s,1H), 7.0–7.6(m,3H). |
| [22] | (2-thienyl) | Na | KBr: 3350, 1765, 1660, 1605 cm$^{-1}$. [α]$_D^{24.5}$ = −62.5 ± 1°. (c=1.00,H$_2$O). | D$_2$O,DSS: 3.52(s,3H), 3.9–4.6(m,2H × 4), 5.13(s, 1H), 5.67(s,1H), 6.9–7.5(m,3H). |

EXAMPLE 10 p-Methoxybenzyl 7β-[D-2-ureido-2-(2-thienyl)acetamido]-7α-methoxy-3-[1-(2-hydroxyethyl)-5-1H-tetrazolyl]thiomethyl-1-dethia-1-oxa-3-cephem-4-carboxylate (Compound No. 24).

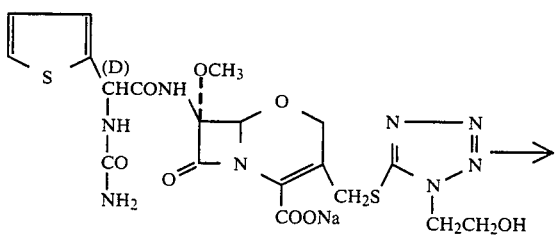

[23]

The sodium salt of the formula [23] (700 mg, 1.22 mM) is dissolved in DMF (10 ml). To the solution are added sodium iodide (0.1 g) and p-methoxybenzyl chloride (2.30 mg), and the mixture is left to stand overnight at room temperature. The reaction mixture is poured into a mixture of ethyl acetate and water. The ethyl acetate layer is separated from the mixture, washed successively with aqueous NaHCO$_3$ solution, water and saturated saline, and dried. After evaporation of the solvent, the residue is dissolved in a minimum amount of methyl ethyl ketone and applied to a column packed with silica gel (20 g, water content: 10%). The column is eluted successively with benzene/ethyl acetate(1:1), ethyl acetate, and methyl ethyl ketone. Evaporation of the fractions eluted with methyl ethyl ketone gives an oily residue, which is dissolved in acetone. The acetone sulution is poured into ethyl ether to precipitate the title compound [24] as a powder. Yield: 490 mg (60%).

IR(KBr): 3460, 3360, 1780, 1715, 1700(sh), 1655 cm$^{-1}$.

UV($\lambda_{max}^{MeOH}$): 228($\epsilon$: 27020), 277($\epsilon$: 11150), 280($\epsilon$: 11370)nn.

NMR(d6-acetone): 3.42(s,3H), 3.77(s,3H), 3.9-4.05(m,2H), 4.2-4.5(m,4H), 4.53(s,2H), 5.07(s,1H), 5.23(s,2H), 5.64(brs,2H), 6.20(d,J=8 Hz,1H), 6.8-7.5(m,8H), 9.29(s,1H).

$[\alpha]_D^{24.5}$: $-90.0°\pm1.3$(c=1, MeOH).

Elementary Analysis($C_{27}H_{30}O_9N_8S_2.\frac{1}{2}H_2O$)

|  | C | H | N | S |
|---|---|---|---|---|
| Calculated (%): | 47.43 | 4.57 | 16.39 | 9.38 |
| Found (%): | 47.27 | 4.31 | 15.96 | 9.10 |

EXAMPLE 11

Pivaloyloxymethyl 7β-[D-2-ureido-2-(2-thienyl)acetamido]-7α-methoxy-3-[1-(2-hydroxyethyl)-5-1H-tetrazolyl]thiomethyl-1-dethia-1-oxa-3-cephem-4-carboxylate (Compound No. 25).

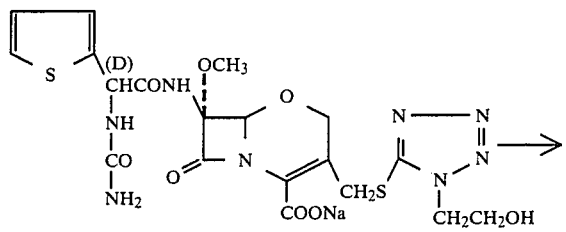

[25]

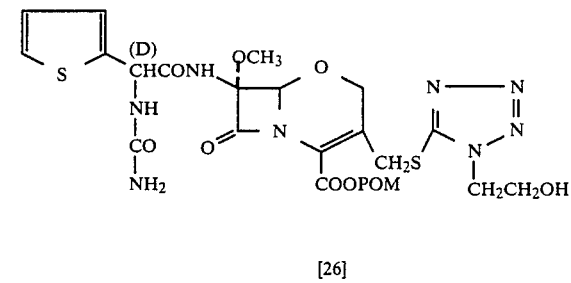

[26]

The sodium salt of the formula [25] (1.5 g, 2.6 mM) is dissolved in DMF (15 ml). To the solution is added pivaloyloxymethyl iodide (755 mg, 3.12 mM) while ice-cooling and the mixture is stirred for 2 hours and 15 minutes. After addition of thiourea (990 mg, 13 mM), the reaction mixture is stirred at room temperature for ten minutes and poured into a mixture of ethyl acetate and water. The organic layer is separated, washed succesively with aqueous NaHCO3 solution, water and saturated saline, and dried. The solvent is evaporated and the residue is purified by column chromatography using silica gel (40 g, water content: 10%). The column is eluted successively with benzene/ethyl acetate(1:1), benzene/ethyl acetate(1:2), ethyl acetate, and methyl ethyl ketone. Evaporation of the solvent from the fractions eluted with methyl ethyl ketone gives an oily residue, which is dissolved in methanol. The methanol solution is poured into ethyl ether to precipitate powdery pivaloyloxymethyl ester of the formula [26]. Yield: 1.11 g (63.7%).

IR(KBr): 3460, 3380, 1783, 1750, 1690(sh), 1655 cm$^{-1}$.

UR($\lambda_{max}^{MeOH}$): 231($\epsilon$: 15230), 283($\epsilon$: 9880)nm.

NMR(d6-acetone): 1.20(s,9H), 3.44(s,3H), 4.00(t,J=6 Hz,2H), 4.25(brs,2H), 4.38(t,J=6 Hz,2H), 4.57(s,2H), 5.10(s,1H), 5.70(brs,2H), 5.89, 6.03(ABq,J=7 Hz,2H), 6.79(d,J=9 Hz), 6.8-7.4(m,4H), 9.50(s,1H).

$[\alpha]_D^{24.5}$: $-75.1°\pm1.2$(c=1, MeOH).

Elementary Analysis($C_{25}H_{32}O_{10}N_8S_2.\frac{1}{2}H_2O$)

|  | C | H | N | S |
|---|---|---|---|---|
| Calculated (%): | 44.31 | 4.91 | 16.53 | 9.46 |
| Found (%): | 44.02 | 4.93 | 16.57 | 9.25 |

EXAMPLE 12

Diphenylmethyl 7β-(D-2-ureido-2-phenylacetamido)-7α-methoxy-3-[1-(2-benzyloxycarbonyloxy)ethyl-5-1H-tetrazolyl]thiomethyl-1-dethia-1-oxa-3-cephem-4-carboxylate (Compound No. 29).

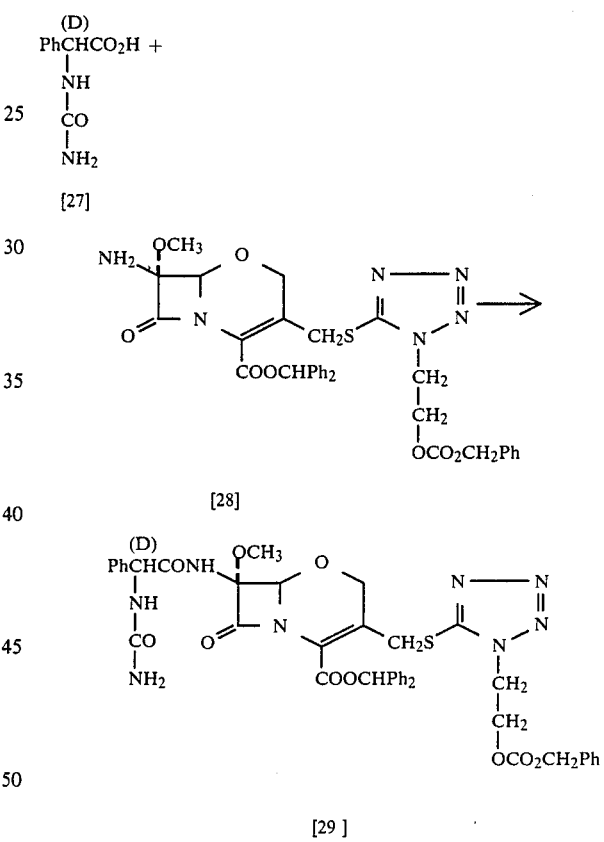

Thionyl chloride (0.89 ml, 12.3 mM) is added at −50° C. to a suspension of the compound of the formula [27] (2 g, 10.3 mM) in acetonitrile (25 ml), and the mixture is allowed to warm up to −10° C. over one hour while stirring. Ethyl ether is then added to the reaction mixture and precipitated powdery substance is collected. This substance is added at −30° C. to a solution of the amine compound [28] (4.62 g, 6.87 mM) and propylene oxide (25 ml) dissolved in DMF (45 ml), and the mixture is stirred for 15 minutes at this temperature and subsequently for one hour while ice-cooling. The reaction mixture is poured into a mixture of ethyl acetate and water. The organic layer is separated, washed successively with aqueous NaHCO3 solution, water and saturated saline, and dried. Evaporation of the solvent from the mixture gives a residue, which is purified by column chromatography using silica gel (40 g, water content: 10%). The column is eluted successively with benzene/ethyl acetate(3:1), benzene/ethyl acetate(1:1) and ethyl acetate. From the fractions eluted with ethyl acetate is obtained powdery amide compound of the formula [29]. Yield: 3.57 g (61.2%).

IR(CHCl₃): 3450, 3350, 3150, 1780, 1750, 1720, 1695, 1650 cm⁻¹.

NMR(CDCl₃+CD₃OD): 3.50(s,3H), 4.10(brs,2H), 4.23(brs,2H), 4.40(s,4H), 4.95(s,1H), 5.06(s,2H), 5.47(s,1H), 6.87(s,1H), 7.2–7.45(m,15H).

EXAMPLE 13

7β-(D-2-Ureido-2-phenylacetamido)-7α-methoxy-3-[1-(2-hydroxyl)ethyl-5-1H-tetrazolyl]thiomethyl-1-dethia-1-oxa-3-cephem-4-carboxylic acid (Compound No. 30).

[29] ⟶

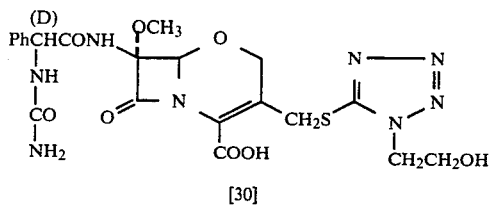

[30]

The diphenylmethyl ester [29] (3.0 g, 3.53 mM) obtained in Example 12 is dissolved in methylenechloride (12 ml). The solution is added at 0° C. to a solution consisting of anhydrous aluminum chloride (1.41 g, 10.6 mM), anisole (7 ml) and nitromethane (19 ml). The mixture is stirred for 1.5 hours and then poured into aqueous NaHCO₃ solution. The aqueous mixture is filtered, and the filtrate is washed with ethyl acetate and methylenechloride. The aqueous layer is acidified with 10% hydrochloric acid, saturated with sodium chloride and extracted with methyl ethyl ketone. The extract is dried over magnesium sulfate. After evaporation of the solvent, the title carboxylic acid [30] is obtained as a residue. Yield: 1.2 g (61.9%).

IR(KBr): 1785, 1770, 1710, 1655, 1635 cm⁻¹.

NMR(d6-DMSO): 3.35(s,3H), 3.75(t,J=6 Hz,2H), 4.23(t,J=6 Hz,2H), 4.33(s,2H), 4.40(s,2H), 5.02(s,1H), 5.49(d,J=9 Hz,1H; singlet after addition of D₂O), 5.60(brd,1H), 6.70(d,J=9 Hz,1H; disappeared by addition of D₂O), 7.2–7.4(m,5H).

[α]$_D^{25.0}$: −95.3°±1.3(c=1.012, MeOH).

The carboxylic acid [30] (1.1 g, 2 mM) is dissolved in aqueous NaHCO₃ solution (NaHCO₃ 160 mg (1.9 mM), H₂O 30 ml). The solution is filtered and the filtrate is lyophilized to obtain corresponding sodium salt [19]. Yield: 1.04 g.

IR(KBr): 3440, 3360, 1765, 1655, 1600 cm⁻¹.

UV(λ$_{max}^{MeOH}$): 226(ε: 12850), 270(ε: 10710)nm.

NMR(D₂O): 3.50(s,3H), 3.8–4.6(m,8H), 5.08(s,1H), 5.37(s,1H), 7.43(brs,5H).

[α]$_D^{25.0}$: −72.6°±1.1(c=1.013, MeOH).

Elementary Analysis(C₂₁H₂₃O₈N₈SNa.2.5H₂O)

|  | C | H | N | S |
|---|---|---|---|---|
| Calculated (%): | 40.98 | 4.58 | 18.20 | 5.21 |
| Found (%): | 41.10 | 4.33 | 17.99 | 4.85 |

The compounds (I) of the invention can also be prepared by reacting the amine of the general formula (IV) with the carboxylic acid of the general formula (V) or its reactive derivative according to any one of the general procedures described below. In the following items (1) to (20), part(s) are by volume with respect to the weight of the starting amine (II).

(1) The amine (IV) wherein R³ is H(1 mol.) is dissolved in water (10 parts) containing NaHCO₃ (2.5 mol.). An acid chloride derivative of the compound (V) (1.1 mol.) is dropwise added thereto, and the mixture is allowed to react at a temperature between −5° C. and room temperature for 30 minutes to 2 hours.

(2) The amine (IV) wherein R³ is H (1 mol.) is reacted with trimethylsilyl chloride (1.2 mol.) in the presence of triethylamine (1.2 mol.). The silyl ester of the compound (IV) thus obtained is combined with an acid chloride of the compound (V) (1.1 mol.) and pyridine (4 mol.) at −30° C., and the mixture is allowed to react for 30 minutes to 2 hours. The silyl ester is then hydrolyzed with an acid.

(3) The amine (IV) (1 mol.) and an acid chloride of the compound (V) (1.2 mol.) is stirred in dichloromethane (20 parts) at −30° to 0° C. for 30 minutes to 2 hours in the presence of picoline (4 mol.).

(4) A mixture of the amine (IV) (1 mol.), an acid chloride of the compound (V) (1.1 mol.), ethyl acetate (10 parts) and triethylamine (1.1 mol.) is stirred at 0° to −20° C. for 30 minutes to 3 hours.

(5) A mixture of the amine (IV) (1 mol.), a mixed anhydride of the compound (V) formed with isobutoxyformic acid (1 mol.), chloroform (10 parts), dimethoxyethane (10 parts) and pyridine (1.5 mol.) is stirred at −5° to 10° C. for 30 minutes to 6 hours.

(6) A mixture of the amine (IV) (1 mol.), a bisanhydride of the compound (V) (1.1 mol.), ethyl acetate (10 parts), 1,2-dichloroethane (10 parts) and N-methylmorpholine (1.5 mol.) is heated under reflux for 10 minutes to 2 hours.

(7) A mixture of the amine (IV) (1 mol.), a mixed anhydride of the compound (V) formed with methanesulfonic acid (1.1 mol.) and pyridine (1.5 mol.) is stirred at temperature increasing from 0° C. to room temperature for 1 to 3 hours.

(8) The amine (IV) (1 mol.) in DMF (5 parts) is reacted with a Vilsmeier reagent consisting of the carboxylic acid (V) and DMF in the presence of dimethylaniline (1.3 mol.) at room temperature for 1 to 5 hours.

(9) The amine (IV) (1 mol.) is reacted in ethyl acetate (10 parts) with a mixed anhydride of the compound (V) formed with diethyl phosphate (1.5 mol.) in the presence of pyridine (1.5 mol.) at 0° to 10° C. for 1 to 5 hours.

(10) The amine (IV) (1 mol.) is reacted with a mixed anhydride of the compound (V) formed with phosphoric acid dichloride (1.1 mol.) in the presence of ethyl acetate (7 parts), dichloromethan (10 parts) and pyridine (1 mol.) at 0° C. to room temperature for 1 to 3 hours.

(11) A mixture of the amine (IV) (1 mol.), lutidine (1.5 mol.), dichloromethane (10 ml) and a mixed anhydride of the compound (V) formed wih monochloro phosphorusdimethylamide (1.1 to 2 mol.) is stirred at 0° to 30° C. for 1 to 4 hours.

(12) A mixture of the amine (IV) (1 mol.), dichloromethane (30 parts), cyanuric chloride (1.1 mol.), pyridine (4 mol.) and the carboxylic acid (V) (1.1 mol.) is stirred at −30° to 10° C. for 30 minutes to 2 hours.

(13) A mixture of the amine (IV) (1 mol.), dichloromethane (3 parts), phosphorus oxychloride (1.1 mol), pyridine (1.5 mol.) and the carboxylic acid (V) (1.1 mol.) is stirred at −10° to 10° C. for 20 minutes to 2 hours.

(14) The amine (IV) (1 mol.) is reacted with trimethylsilyl chloride to form the corresponding N-trimethylsilyl amine. The N-silyllated compound (1 mol.) is treated with a mixture of phosphorus oxychloride (1.5 mol.), the carboxylic acid (V) (1.2 mol.), pyridine (4 mol.) and dichloromethane (5 parts) at 0° C. to room temperature for 30 minutes to 2 hours.

(15) A mixture of the amine (IV) (1 mol.), dichloromethane (8 parts), thionyl chloride (1.5 mol.), pyridine (2.5 mol.) and the carboxylic acid (V) (1.1 mol.) is stirred at −30° to 0° C. for 1 to 5 hours.

(16) A mixture of the amine (IV) (1 mol.), dichloromethane (5 parts), trifluoroacetic anhydride (1.5 mol.), pyridine (3 mol.) and the carboxylic acid (V) (1.5 mol.) is stirred at 0° C. to room temperature for 1 to 5 hours.

(17) A mixture of the amine (IV) (1 mol.), dichloromethane (10 parts), diethyl bromo phosphate (1.2 mol.), N-methylmorpholine (2.5 mol.) and the carboxylic acid (V) (1.2 mol.) is stirred at 0° to 30° C. for 1 to 3 hours.

(18) A mixture of the amine (IV) (1 mol.), dichloromethane (3 parts), 1,3,5-tripyridiniumtriazine trichloride (4 mol.) and the carboxylic acid (V) (1.1 mol.) is stirred at −10° to 10° C. for 1 to 5 hours.

(19) A mixture of the amine (IV) (1 mol.), CCl₄ (30 parts), N-methylmorpholine (1.5 mol.), trisdiethylaminophosphine (1.1 mol.) and the carboxylic acid (V) (1.1 mol.) is allowed to stand at −20° to 10° C. for 1 to 5 hours.

(20) A mixture of the amine (IV) (1 mol.), chloroform (3 parts), toluene (1 part), picoline (2 mol.), oxalyl chloride (1 mol.) and the carboxylic acid (V) (1.1 mol.) is stirred at −50° to 10° C. for 10 minutes to 2 hours.

EXAMPLE 14

7β-[D-2-Ureido-2-(p-hydroxyphenyl)acetamido]-7α-methoxy-3-[1-(2-hydroxyethyl)-5-1H-tetrazolyl]thiomethyl-1-dethia-1-oxa-3-cephem-4-carboxylic acid, and diphenylmethyl ester and sodium salt thereof.

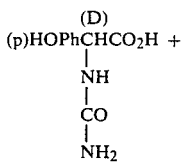

[31]

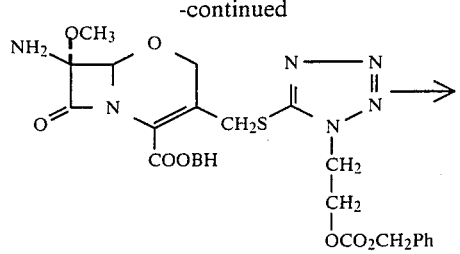

[32]

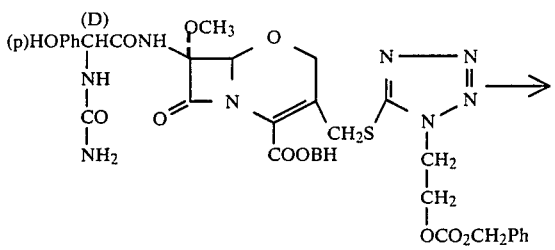

[33]

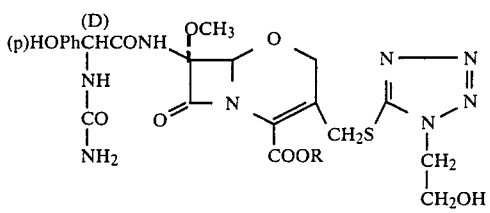

[34]

The carboxylic acid of the formula [31] (1.5 g, 7.14 mM) is suspended in acetonitrile (15 ml). After addition of thionylchloride (1.02 g, 8.56 mM), the suspension is stirred at −20° C. for 40 minutes and evaporated under reduced pressure to remove the solvent. To the residue is added at −40° C. a solution of the amine compound of the formula [32] (3.2 g, 4.76 mM) and propylene oxide (15 ml) dissolved in DMF (30 ml). The mixture is stirred at 0° C. for 2 hours and then poured into ethyl acetate. The mixture is washed successively with aqueous NaHCO₃ solution, water and saturated saline, and dried. After evaporation of the solvent from the mixture, the residue is purified by column chromatography using silica gel (50 g, water content: 10%). The column is eluted with benzene/ethyl acetate (1:1–1:2), ethyl acetate, and methyl ethyl ketone. Fractions eluted with methyl ethyl ketone is concentrated and the residue is dissolved in acetone. The acetone layer is poured into ethyl ether to precipitate the desired diphenylmethyl ester of the formula [33] as a powder. Yield: 1.5 g(35.7%).

IR(CHCl₃): 3420, 3340, 1780, 1740, 1710, 1680, 1640 cm⁻¹.

NMR(CDCl₃/CD₃OD=1/1): 3.50(s,3H), 4.0–4.4(m,4H), 4.47(s,4H), 5.05(s,3H), 5.37(s,1H), 6.77(d,J=9 Hz,2H), 6.83(s,1H), 7.3–7.6(m,17H).

Anhydrous aluminum chloride (1.39 g, 10.4 mM) is dissolved in anisole (7 ml) and nitromethane (26 ml). To the mixture is added while ice-cooling the diphenylmethyl ester [33] (1.5 g, 1.73 mM), and the mixture is stirred for one hour at this temperature. The reaction mixture is poured into a mixture of aqueous NaHCO₃ solution and ethyl acetate, and the precipitated substance is filtered off. The aqueous NaHCO₃ layer is separated from the filtrate and washed with methylenechloride. The aqueous layer is acidified with hydrochloric acid and passed through an adsorption column packed with HP-20 (about 100 ml). The column is eluted with 40% methanol and the eluate is evaporated under reduced pressure to obtain the title carboxylic acid [34](R=H) as a crystal. Yield: 710 mg (72.5%). m.p.: 177°–178.5° C. (with decomposition).

IR(KBr): 3450, 3320, 1765, 1748, 1710, 1665, 1645(sh), 1630 cm⁻¹.

NMR(CDCl₃/d4-MeOH=¼): 3.47(s,3H), 3.95(t,J=6 Hz,2H), 4.25(s,2H), 4.40(t,J=6 Hz,2H), 4.42(s,2H), 6.75(d,J=9 Hz,2H), 7.28(d,J=9 Hz,2H).

Elementary Analysis ($C_{21}H_{24}O_9N_8S \cdot 1.5H_2O$)

|  | C | H | N | S |
|---|---|---|---|---|
| Calculated (%): | 42.64 | 4.60 | 18.94 | 5.42 |
| Found (%): | 42.82 | 4.47 | 19.21 | 5.29 |

The carboxylic acid [34] (R=H)(660 mg, 1.17 mM) is dissolved in aqueous NaHCO₃ solution (NaHCO₃ 93 mg (1.11 mM), water 30 ml), and the solution is filtered. The filtrate is lyophilized to give the desired sodium salt of the formula [34] (R=Na). Yield: 690 mg.

IR(KBr): 3440, 3360, 1765, 1655, 1605 cm⁻¹.
UV($\lambda_{max}^{MeOH}$): 227.5($\delta$=21200), 273($\delta$=11050)nm.
NMR(D₂O): 3.52(s,3H), 3.8–4.6(m,8H), 5.10(s,1H), 5.30(s,1H), 6.90(d,J=9 Hz,2H), 7.33(d,J=9 Hz,2H).
$[\alpha]_D^{23.0}$=−68.0±1.1° (c=1.008, H₂O).

Elementary Analysis ($C_{21}H_{23}O_9N_8SNa \cdot H_2O$)

|  | C | H | N | S |
|---|---|---|---|---|
| Calculated (%): | 41.72 | 4.17 | 18.54 | 5.30 |
| Found (%): | 41.79 | 4.16 | 18.92 | 5.35 |

EXAMPLE 15

7β-[D-2-(2-Chloroethylureido)-2-(2-thienyl)acetamido]-7α-methoxy-3-[1-(2-hydroxyethyl)-5-1H-tetrazolyl]thiomethyl-1-dethia-1-oxa-3-cephem-4-carboxylic acid (Compound No. 38).

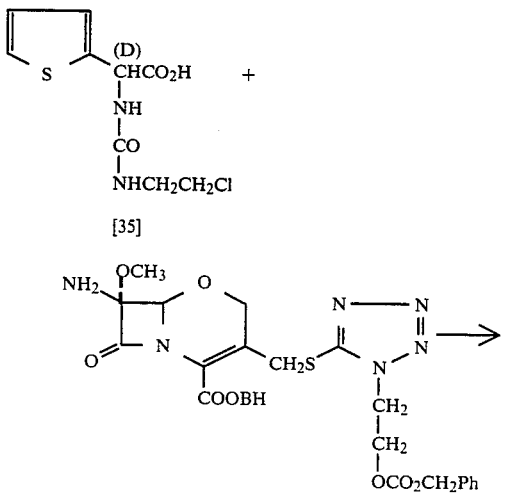

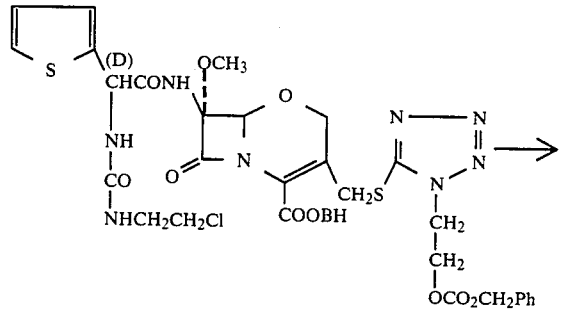

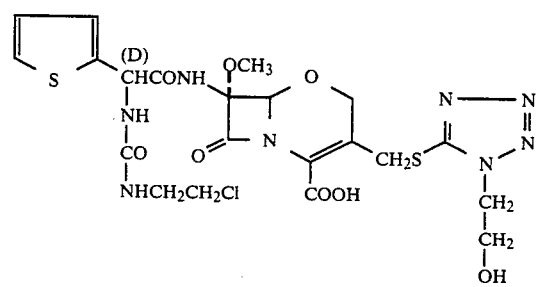

The carboxylic acid of the formula [35] (5.8 g, 22.0 mM) is suspended in acetonitrile (45 ml). After addition of thionylchloride (2.63 g, 22.0 mM), the suspension is stirred at between −40° C. and −35° C. for 50 minutes and evaporated under reduced pressure to remove the solvent. To the residue is added at the same temperature as above a solution of the amine compound of the formula [36] (7.74 g, 115 mM) and propylene oxide (30 ml) dissolved in DMF (30 ml). The mixture is stirred at 0° C. for one hour and then poured into ethyl acetate. The mixture is washed successively with aqueous NaHCO₃ solution, water and saturated saline, and dried. After evaporation of the solvent from the mixture, the residue is purified by chromatography over silica gel (water content: 10%) using benzene/ethyl acetate (3:1–1:1) as the eluent. Fractions containing the desired compound are combined and concentrated under reduced pressure. The resultant residue is dissolved in acetone and the solution is poured into ethyl ether to precipitate the diphenylmethyl ester of the formula [37]. Yield: 9.0 g (85.2%).

IR(CHCl₃): 3370, 1780, 1740, 1720, 1650 cm⁻¹.
NMR(CDCl₃—CD₃OD): 3.50(s,3H), 3.35–3.8(m,4H), 4.15(brs,2H), 4.39(s,6H), 5.00(s,1H), 5.05(s,2H), 5.87(s,1H), 6.30(brs,1H), 6.88(s,1H), 6.8–7.6(m,18H).

Anhydrous aluminum chloride (7 g) is dissolved in anisole (45 ml) and nitromethane (90 ml). To the mixture is added while ice-cooling a solution of the diphenylmethyl ester [37] (6.4 g, 6.98 mM) dissolved in dichloromethane (60 ml). The mixture is stirred for one hour while ice-cooling and then poured into a mixture of aqueous NaHCO₃ solution and ice, and the precipitated substance is filtered off. The filtrate is adjusted to pH 5.0 with hydrochloric acid and washed with ethyl acetate. The aqueous layer is readjusted to pH 1 with hydrochloric acid, saturated with sodium chloride and extracted with ethyl acetate. The extract is dried and evaporated in vacuo to remove the solvent. The title compound of the formula [38] is obtained as a powdery residue. Yield: 3.52 g (81.8%).

IR(nujol): 3300(br), 1780, 1700, 1660(sh), 1640 cm$^{-1}$.
NMR(d6-acetone): 3.44(s,3H), 3.3–3.6(m,4H), 3.95(t,J=6 Hz, 2H), 4.29(s,2H), 4.40(t,J=6 Hz,2H), 4.53(s,2H), 5.07(s,1H), 5.95(d,J=9 Hz,1H), 6.29(br,1H), 6.67(d,J=9 Hz,1H), 6.8–7.3(m,3H), 8.57(s,1H).

EXAMPLE 16

Diphenylmethyl 7β-[D-2-(2-iodoethylureido)-2-(2-thienyl)acetamido]-7α-methoxy-3-[1-(2-benzyloxycarbonyloxy)ethyl-5-1H-tetrzolyl]thiomethyl-1-dethia-1-oxa-3-cephem-4-carboxylate [Compound No. 39].

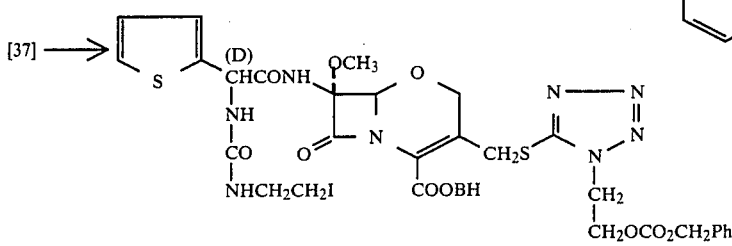

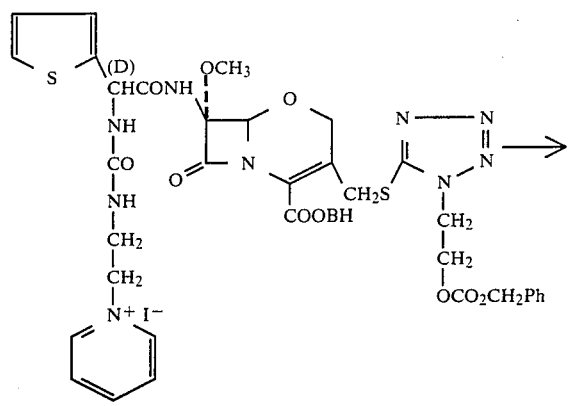

The compound of the formula [37] (2.5 g, 2.73 mM) obtained in Example 15 and sodium iodide (1.24 g, 8.30 mM) are suspended in methyl ethyl ketone and the suspension is heated at 80° to 90° C. for 5.5 hours. The reaction mixture is poured into ethyl acetate, washed with water, dried and evaporated to dryness under reduced pressure. The resulting oily residue is purified by chromatography over silica gel (water content: 10%) using benzene/ethyl acetate (3:1–1:1) as the eluent to obtain the title compound of the formula [39] as a powder. Yield: 1.25 g (45.5%).

IR(CHCl$_3$): 3370(br), 1790, 1730, 1665 cm$^{-1}$.
NMR(CDCl$_3$): 3.07(t,J=6 Hz,2H), 3.33(t,J=6 Hz,2H), 3.43(s,3H), 4.15(brs,2H), 4.40(brs,6H), 4.97(s,1H), 5.08(s,2H), 6.05(br,2H), 6.7–7.6(m).

EXAMPLE 17

7β-[D-2-(2-Pyridinioethylureido)-2-(2-thienyl)acetamido]-7α-methoxy-3-[1-(2-hydroxyethyl)-5-1H-tetrazolyl]thiomethyl-1-dethia-1-oxa-3-cephem-4-carboxylate (Compound No. 41).

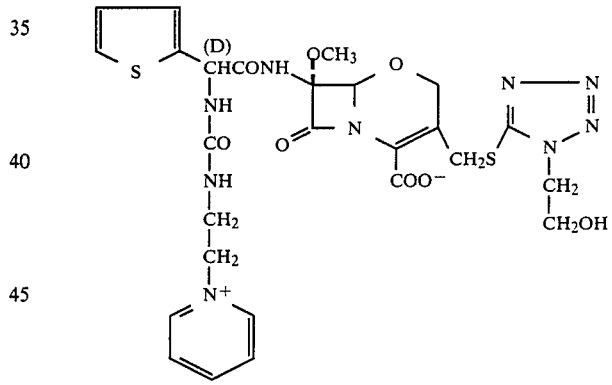

The compound of the formula [39] (1.25 g, 1.48 mM) prepared in Example 16 is dissolved in acetonitrile (18 ml). After addition of pyridine (0.6 ml), the solution is heated to 55°–60° C. for 8 hours. The reaction mixture is evaporated in vacuo to remove the solvent. The residue is washed with ethyl ether and chromatographed over silica gel (water content: 10%) using a mixture of dichloromethane and methanol (6:1–5:1) as the eluent to obtain the intermediate compound of the formula [40] as a powder. Yield: 630 mg (46.7%).

IR(CHCl$_3$): 3300(br), 1780, 1750, 1710, 1660 cm$^{-1}$.
NMR(CDCl$_3$/CD$_3$OD=3/1): 3.43(s,3H), 3.73(brs,2H), 4.72(brs,2H), 4.18(s,2H), 4.50(s,4H), 4.60(s,2H), 5.10(s,3H), 5.56(s,1H), 6.89(s,1H), 6.9–7.5(m,18H), 7.8–8.9(m,5H).

Anhydrous aluminum chloride (1.0 g) is dissolved with stirring in anisole (45 ml) and nitromethane (10 ml)

at room temperature. The mixture is added while ice-cooling to a stirred solution of the intermediate compound [40] (600 mg) dissolved in nitromethane (6 ml) and dichloromethane (6 ml). The mixture is stirred for 45 minutes under nitrogen gas and poured into ice-cooled aqueous $NaHCO_3$ solution. Precipitated solids are filtered off. An aqueous layer is separated from the filtrate, washed with dichloromethane, adjusted to pH 5.5 with hydrochloric acid and washed again with ethyl acetate. The aqueous layer is readjusted to pH 1 with hydrochloric acid and evaporated under reduced pressure to remove the solvent and carbon dioxide. The residue is adsorbed to HP-20 and eluted with 20% and 50% aqueous methanol solutions. The eluate is lyophilized to obtain the title compound of the formula [41]. Yield: 290 mg (79.6%).

IR(KBr): 3280(br), 1770, 1665, 1635, 1605 $cm^{-1}$.

NMR($D_2O$): 3.43(s,3H), 3.73(brs,2H), 4.45(brs,2H), 3,92(t,J=6 Hz,2H), 4.50(t,J=6 Hz,2H), 3.95(s,2H), 4.15(brs,2H), 5.10(s,1H), 5.50(s,1H), 6.9–7.4(m,3H), 7.9–8.8(m,5H).

What is claimed is:

1. A 7β-ureidoacetamido-7α-methoxy-3-[1-(2-hydroxyethyl)-1H-tetrazol-5-yl]thiomethyl-1-dethia-1-oxa-3-cephem-4-carboxylic acid derivative represented by the following formula:

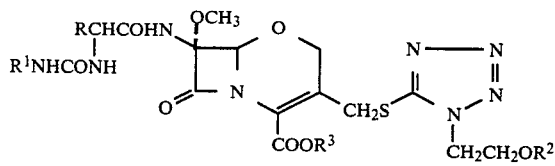

wherein R is aryl or heteroaryl; $R^1$ is hydrogen or alkyl optionally substituted by halogen or pyridinium; $R^2$ is hydrogen or a hydroxy-protecting group; and $R^3$ is hydrogen, a light metal, or a carboxy-protecting group.

2. A compound as claimed in claim 1 wherein R is phenyl, hydroxyphenyl, furyl, or thienyl.

3. A compound as claimed in claim 1 wherein $R^1$ is hydrogen, methyl, ethyl, 2-chloroethyl, 2-iodoethyl, or pyridinium ethyl.

4. A compound as claimed in claim 1 wherein $R^2$ is hydrogen.

5. A compound as claimed in claim 1 wherein $R^2$ is benzyloxycarbonyl, p-methylbenzyloxycarbonyl, acetyl, or haloacetyl.

6. A compound as claimed in claim 1 wherein $R^3$ is hydrogen, sodium, potassium, diphenylmethyl, acetoxymethyl, 1-(ethoxycarbonyloxy)ethyl, or pivaloyloxymethyl.

7. Any one of the following compounds:
diphenylmethyl 7β-[2-ureido-2-(2-thienyl)acetamido]-7α-methoxy-3-[1-(2-benzyloxycarbonyloxyethyl)-5-1H-tetrazolyl]thiomethyl-1-dethia-1-oxa-3-cephem-4-carboxylate, 7β-[2-ureido-2-(2-thienyl)acetamido]-7α-methoxy-3-[1-(2-hydroxyethyl)-5-1H-tetrazolyl]thiomethyl-1-dethia-1-oxa-3-cephem-4-carboxylic acid,
diphenylmethyl 7β-[2-(3-methylureido)-2-(2-carbobenzoxyaminothiazol-4-yl)acetamido]-7α-methoxy-3-[1-(2-p-methylbenzyloxycarbonyloxyethyl)-5-1H-tetrazolyl]thiomethyl-1-dethia-1-oxa-3-cephem-4-carboxylate,
7β-[2-(3-methylureido)-2-(2-aminothiazol-4-yl)acetamido]-7α-methoxy-3-[1-(2-hydroxyethyl)-5-1H-tetrazolyl]-thiomethyl-1-dethia-1-oxa-3-cephem-4-carboxylic acid,
diphenylmethyl 7β-[2-(3-methylureido)-2-(2-thienyl)acetamido]-7α-methoxy-3-[1-(2-p-methylbenzyloxycarbonyloxyethyl)-5-1H-tetrazolyl]thiomethyl-1-dethia-1-oxa-3-cephem-4-carboxylate,
7β-[2-(3-methylureido)-2-(2-thienyl)acetamido]-7α-methoxy-3-[1-(2-hydroxyethyl)-5-1H-tetrazolyl]thiomethyl-1-dethia-1-oxa-3-cephem-4-carboxylic acid,
diphenylmethyl 7β-[2-ureido-2-(2-thienyl)acetamido]-7α-methoxy-3-[1-(2-hydroxyethyl)-5-1H-tetrazolyl]-thiomethyl-1-dethia-1-oxa-3-cephem-4-carboxylate,
pivaloyloxymethyl 7β-[2-ureido-2-(2-thienyl)acetamido]-7α-methoxy-3-[1-(2-hydroxyethyl)-5-1H-tetrazolyl]thiomethyl-1-dethia-1-oxa-3-cephem-4-carboxylate,
sodium 7β-(2-ureido-2-phenylacetamido)-7α-methoxy-3-[1-(2-hydroxyethyl)-5-1H-tetrazolyl]thiomethyl-1-dethia-1-oxa-3-cephem-4-carboxylate,
sodium 7β-[2-ureido-2-(p-hydroxyphenyl)acetamido]-7α-methoxy-3-[1-(2-hydroxyethyl)-5-1H-tetrazolyl]-thiomethyl-1-dethia-1-oxa-3-cephem-4-carboxylate,
sodium 7β-[2-ureido-2-(2-furyl)acetamido]-7α-methoxy-3-[1-(2-hydroxyethyl)-5-1H-tetrazolyl]thiomethyl-1-dethia-1-oxa-3-cephem-4-carboxylate,
sodium 7β-[2-ureido-2-(2-thienyl)acetamido]-7α-methoxy-3-[1-(2-hydroxyethyl)-5-1H-tetrazolyl]thiomethyl-1-dethia-1-oxa-3-cephem-4-carboxylate,
p-methoxybenzyl 7β-[2-ureido-2-(2-thienyl)acetamido]-7α-methoxy-3-[1-(2-hydroxyethyl)-5-1H-tetrazolyl]-thiomethyl-1-dethia-1-oxa-3-cephem-4-carboxylate,
diphenylmethyl 7β-(2-ureidio-2-phenylacetamido)-7α-methoxy-3-[1-(2-benzyloxycarbonyloxyethyl)-5-1H-tetrazolyl]thiomethyl-1-dethia-1-oxa-3-cephem-4-carboxylate,
7β-(2-ureido-2-phenylacetamido)-7α-methoxy-3-[1-(2-hydroxyethyl)-5-1H-tetrazolyl]thiomethyl-1-dethia-1-oxa-3-cephem-4-carboxylic acid,
diphenylmethyl 7β-[2-ureido-2-(p-hydroxyphenyl)acetamido]-7α-methoxy-3-[1-(2-benzyloxycarbonyloxyethyl)-5-1H-tetrazolyl]thiomethyl-1-dethia-1-oxa-3-cephem-4-carboxylate, or
sodium 7β-[2-ureido-2-(p-hydroxyphenyl)acetamido]-7α-methoxy-3-[1-(2-hydroxyethyl)-5-1H-tetrazolyl]-thiomethyl-1-dethia-1-oxa-3-cephem-4-carboxylate.

8. An antibacterial composition comprising an effective amount of the compound as claimed in claim 1 and conventional carrier.

9. A method for combating bacteria which comprises bringing an effective amount of the compound as claimed in claim 1 to contact with the bacteria.

* * * * *